United States Patent
Chaiken et al.

(10) Patent No.: US 6,461,594 B1
(45) Date of Patent: Oct. 8, 2002

(54) PHOTOCHROMIC MATERIALS SUITABLE FOR COSMETIC AND SUNBLOCKING EFFECTS

(75) Inventors: Joseph Chaiken, Fayetteville, NY (US); Robert R. Birge, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 09/492,208

(22) Filed: Jan. 27, 2000

Related U.S. Application Data

(60) Provisional application No. 60/117,521, filed on Jan. 28, 1999.

(51) Int. Cl.[7] .................................................. A61K 7/42
(52) U.S. Cl. ........................................ 424/59; 514/769
(58) Field of Search ............................ 424/59; 514/169

(56) References Cited

U.S. PATENT DOCUMENTS

| | | | |
|---|---|---|---|
| 4,711,815 A | * 12/1987 | Yoshike et al. | 428/411.1 |
| 5,628,934 A | * 5/1997 | Ohno et al. | 252/586 |
| 5,691,091 A | * 11/1997 | Chaiken et al. | 430/19 |
| 5,922,843 A | * 7/1999 | Tan et al. | 530/350 |
| 6,190,677 B1 | * 2/2001 | Remy | 424/401 |
| 6,224,884 B1 | * 5/2001 | Remy | 424/401 |

FOREIGN PATENT DOCUMENTS

WO           9312195       * 6/1993

* cited by examiner

*Primary Examiner*—Jose' G. Dees
*Assistant Examiner*—Michael A. Williamson
(74) *Attorney, Agent, or Firm*—Wall Marjama & Bilinski LLP

(57) ABSTRACT

Tungsten and molybdenum oxide, and oxides of other metals and bronzes derived from such oxides, constitute a broad class of materials having applications as photochromic sunblock/cosmetics. These materials are well known in the prior art in the context of photochromic optical data storage media and they offer an excellent match with the very properties needed for cosmetic applications. The invention relates to the adaptation of the class of tungsten and molybdenum oxide photochromics to sunblocking/dosimetry, energy storage, and cosmetic coloration. In addition, certain naturally occurring proteins which exhibit the necessary photochromism can also be used alone for the same purpose or with the oxide systems described above.

1 Claim, No Drawings

PHOTOCHROMIC MATERIALS SUITABLE FOR COSMETIC AND SUNBLOCKING EFFECTS

This application claims of the benefit of Provisional application No. 60/117,521 filed Jan. 28, 1999.

BACKGROUND AND SUMMARY OF THE INVENTION

The present invention relates in general to cosmetic materials, and more specifically to photochromic materials which are suitable for use in cosmetic and related formulations.

Coloration has been employed as a cosmetic device since before recorded time. Materials and methods for achieving predictable and safe cosmetic coloration are being continually explored and improved as evidenced by the large and expanding world wide cosmetic business. Materials which change color under the influence of light, i.e. photochromics, can be designed on the molecular level to interact with light to maintain, or even evolve a particular coloration. These materials can be designed to maintain a particular cosmetic look as the ambient lighting changes or as the user moves from place to place. It may be advantageous for the photochemic response to be reversible. The influence of water can be anticipated and pH balance must be incorporated into the overall system design. It would be advantageous to design a class of materials for which ambient office light, or highly directed light such as in a tanning booth, or even laser light, could be utilized, each creating and imparting a particular predictable cosmetic look. There are, of course, many organic photochromic materials. However, by necessity, to have a strong absorption feature in the visible part of the spectrum which could be the basis for an effective cosmetic coloration system, the molecular structure often contains a delocalized pi electron system. Molecules having bonding features associated with such electronic structure, e.g. polycyclic aromatic hydrocarbons, coal tar products, azo dyes, quinoline, and like molecules with or without fused heterocycles, are often carcinogenic and so less desirable or unacceptable as candidates for use as cosmetics. Many types of organic molecules penetrate the skin barrier and so pose increased toxicity risk. This is a major problem because it would require more complicated testing and evaluation to establish the risk of such materials.

Inorganic materials are well known which, because of their insolubility in water or lipid and their relatively large particle size, do not penetrate the stratum corneum to any major extent. For example, rouge, being iron oxide, and titanium dioxide are two widely used oxides with well established safety history. In fact, most metal oxides, with the possible exception of those used close to the eyes, are more likely ingested, and therefore dangerous if the particles are breathed. There is, therefore, a negligible risk if the oxides are immobilized in a cosmetic formulation.

The objective of the present invention is to identify metal oxides, metal bronzes, and protein based photochromic systems (materials) which combine novel cosmetic properties with sunblocking. Photochromic systems have novel applications in cosmetics because the coloration they supply can be accented and softened and otherwise manipulated by the application of light, allowing greater control and range of effect than for a single color application. Conventional coloration, i.e. rouge, can only be manipulated by mechanical means, i.e. rubbing and spreading. In addition to using these materials for their pleasing coloration effects, they can also be used as an actinometer/dosimeter that a person can use to gauge his/her exposure to bright sunlight or in other tanning/burning settings.

The present invention is based upon the use of the intrinsic photochromic properties of certain solid transition metal oxides for cosmetic and sunblocking effects. The solid metal oxides suitable for use in this invention are those which undergo photoinduced and thermoenhanced loss of gas phase $O_2$ to produce mixed valence oxides and include $WO_3$, $V_2O_5$, $TiO_2$ and $MoO_3$. Any other solid transition metal oxide which exhibits these characteristics is included within the scope of this invention. A particular oxide can be operationally established for any possible choice of oxide by exposing a possible candidate oxide to blue-green or shorter wavelength light under vacuum and observing whether a color change occurs. In some cases, the oxide is doped with an alkali metal ion or proton to enhance the color change.

As described above, tungsten and molybdenum oxide, and oxides of other metals, and bronzes derived from such oxides, constitute a broad class of materials having potential application as photochromic sunblock/cosmetics. These materials are well known in the context of photochromic optical data storage media and they offer an excellent match with the very properties needed for cosmetic applications. The present invention relates to the adaptation of the class of tungsten and molybdenum oxide photochromics to sunblocking/dosimetry, energy storage, and cosmetic coloration.

In a further embodiment, certain naturally occurring proteins which exhibit the necessary photochromism can also be used with the oxide systems of the present invention described above.

DETAIL DESCRIPTION OF THE INVENTION

The present invention identifies novel photochromic materials which are appropriate for cosmetic application. There are many inorganic and organic photochromic materials but only a select number offer truly pleasing coloration effects and are also suitably nontoxic. Suitable inorganic materials which may be used in the present invention include tungsten and molybdenum oxide, tungsten and molybdenum bronzes derived from proton (i.e. hydrogen), alkali metal and other metal donors, as well as organic materials such as the visual pigments known as the rhodopsins which are uniquely suited for such application. These materials combine the necessary spectroscopic and physical properties to allow sunblocking and coloration with a notable lack of toxicity. They are robust in that they can be used in encapsulated form and that they can be used separately or combined to give interesting variations in cosmetic and sunblocking effect.

More specifically, tungsten and molybdenum oxide (either alone or in combination with certain other oxides including but not limited to titanium dioxide, aluminum oxide and silicon dioxide), and tungsten and molybdenum bronzes derived from hydrogen, alkali metals and other metal donors (either alone or in combination with certain other oxides including but not limited to titanium dioxide, aluminum oxide and silicon dioxide), each constitute a broad class of materials having application as photochromic sunblock/cosmetics. These oxides are incorporated into a suitable cosmetic formulation and applied to the skin as a cream or liquid to form a coating or layer on the skin.

An example of the theory or mechanism which is involved in the present invention can be illustrated for the transition metal oxide $WO_3$. The reaction which occurs during cosmetic coloration is when $WO_3$ is exposed to blue-green light and IR light, which results in a change in color of the layer from bright yellow to dark blue with the reaction being described in equation 1:

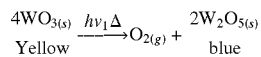

In its blue color form, the oxide is illustrated in equation 1 as $W_2O_{5(s)}$. Because the $WO_3$ is the thermodynamic ground state for the tungsten-oxygen system, the reverse action is easily thermally driven and is illustrated by equation 2:

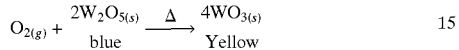

These equations refer to oxygen being transferred between solid and gas phases, but is also possible to use other types of oxygen donors and acceptors. This mechanism is more fully described in U.S. Pat. No. 5,691,091 to Chaiken et al. which is incorporated herein by reference. In addition to the above, it is also possible to manipulate the coloration by interaction with proton donors. This concept is more fully described in U.S. Pat. No. 4,711,815, Yoshiike et al. which is incorporated herein by reference.

Bacteriorhodopsin is a protein which is isolated from a salt marsh bacterium called Halobacterium salinarium. This protein can be chemically modified by adding organic cations and other analog chromophores or through genetic engineering. We have examined four mutants and two chemically modified samples which have significant potential for this application. Because the protein has 8 tryptophan, 11 tyrosine, and 13 phenylalanine residues, it exhibits strong absorption in the 180–330 nm region which provides excellent blocking of UV radiation in this region. The salient characteristic of the protein, however, is a chromophore with absorption extends from 350–630nm, and which changes with the absorption of light. Via chemical and genetic modifications, the nature of this change, and the lifetime of the change, can be adjusted throughout the visible region of the spectrum and adjusted throughout the visible region of the spectrum and adjusted with respect to the time scale of the effect. In the simplest form, this protein can be viewed as nontoxic, and being compatible with the chemical conditions normally expected in cosmetic formulations, these naturally occurring and chemically modified proteins have a proton pumping capacity that allows them to interact photo and electrochemically with the tungsten oxide system.

A more complete understanding of photochromic mechanism of the protein is set forth in the article Protein-Based Computers by Robert R. Birge: Scientific American, March 1995, Vol. 272, No. 3 pp 90–95 and U.S. patent application "Analog Bacteriorhodopsin Molecules" Ser. No. 08/731,328, both of which are incorporated herein by reference.

The following example illustrates a hair conditioner formulation according to the concept of the present invention.

EXAMPLE

The following three components identified as A, B and C, respectively are blended together to form a hair conditioner which is in the form of a viscous fluid:

A.
   0.3 g. of powder thickener available from Jaguar under the tradename HP-8 COS
   0.6 g. of powder thickener available from Jaguar under the tradename C-14.
   The thickeners are mixed with 65 g. of dionized water.

B.
   5.0 g. of Dow Corning 244 silicone fluid
   20.0 g. of glycerin
   5.0 g. of Dow Corning 8220 silicone fluid
   The above are mixed together.

C.
   3.1 g. of bacteriorhodopsin wild type (fluid)
   1.0 g. of liquid germazide MPB available from Collabrative Laboratories.

Components A and B are each separately heated to 70° C. and then mixed together in a flask. The flask was then cooled in an ice bath to 25° C. and component C added to the flask. The resulting mixture was a viscous fluid. The viscous fluid which functions as an all day hair conditioner was then applied to the hair of a human subject having brown hair. The area of the hair receiving the application of the viscous fluid took on a red color, which upon exposure to ambient radiation returned the subject's hair to its normal brown color in about 30 minutes.

While this invention has been explained with reference to the use of materials disclosed herein, it is not confined to the details set forth and this invention is intended to cover any modifications and changes as may come within the scope of the following claims:

What is claimed is:

1. A method of creating a cosmetic or sun blocking effect on the human skin which comprises:

(a) providing a photochromic material which is isolated from the purple membrane protein of halobacterium salinarium (b) applying said material to the human skin in preselected locations; and (c) exposing said material to activating light to produce a color change in said material.

\* \* \* \* \*